United States Patent
Schoen et al.

(10) Patent No.: US 11,707,080 B2
(45) Date of Patent: Jul. 25, 2023

(54) INFANT FORMULA WITH SPECIAL LIPID ARCHITECTURE FOR IMPROVING POSTNATAL GROWTH OF INFANTS BORN BY CAESAREAN SECTION

(71) Applicant: N.V. Nutricia, Zoetermeer (NL)

(72) Inventors: Stefanie Schoen, Utrecht (NL); Dennis Stanley Acton, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 17/775,889

(22) PCT Filed: Dec. 4, 2020

(86) PCT No.: PCT/EP2020/084633
§ 371 (c)(1),
(2) Date: May 11, 2022

(87) PCT Pub. No.: WO2021/110917
PCT Pub. Date: Jun. 10, 2021

(65) Prior Publication Data
US 2022/0386675 A1    Dec. 8, 2022

(30) Foreign Application Priority Data
Dec. 5, 2019 (EP) .................... 19213825

(51) Int. Cl.
*A23L 33/00* (2016.01)
*A23L 33/12* (2016.01)
*A23L 33/17* (2016.01)
*A61P 3/04* (2006.01)

(52) U.S. Cl.
CPC ............... *A23L 33/40* (2016.08); *A23L 33/12* (2016.08); *A23L 33/17* (2016.08); *A61P 3/04* (2018.01)

(58) Field of Classification Search
CPC .......... A23L 33/40; A23L 33/12; A23L 33/17; A23L 33/00; A23L 33/115; A61P 3/04; A61K 31/20; A61K 31/201; A61K 31/202; A61K 31/23; A61K 31/688
See application file for complete search history.

(56) References Cited

U.S. PATENT DOCUMENTS 11,389,403 B2 *   7/2022  Van Der Beek ....... A61K 35/66

FOREIGN PATENT DOCUMENTS

WO      2012/173467 A1   12/2012
WO      2017/064304 A1    4/2017

OTHER PUBLICATIONS

Huh et al: "Delivery by caesarean section and risk of obesity in preschool age children: a prospective cohort study", Archives of Disease in Childhood, vol. 97, No. 7, May 23, 2012 (May 23, 2012), pp. 610-616, XP055720436, ISSN: 0003-9888, DOI: 10.1136/archdischild-2011-301141.
Mesquita et al: "Cesarean Section Is Associated with Increased Peripheral and Central Adiposity in Young Adulthood: Cohort Study", PLOS ONE, vol. 8, No. 6, Jun. 27, 2013 (Jun. 27, 2013), p. e66827, XP055720435, DOI: 10.1371/journal.pone.0066827.
Mueller et al: "Prenatal exposure to antibiotics, cesarean section and risk of childhood obesity", International Journal of Obesity, Newman Publishing, London, GB, vol. 39, No. 4, Oct. 9, 2014 (Oct. 9, 2014), pp. 665-670, XP036971756, ISSN: 0307-0565, DOI: 10.1038/1JO.2014.180 [retrieved on Oct. 9, 2014].

* cited by examiner

*Primary Examiner* — Aradhana Sasan
(74) *Attorney, Agent, or Firm* — N.V. Nederlandsch Octrooibureau

(57) ABSTRACT

The present invention relates to formulae for infants born via Caesarean section for improving the postnatal growth trajectory or body development.

13 Claims, No Drawings

INFANT FORMULA WITH SPECIAL LIPID ARCHITECTURE FOR IMPROVING POSTNATAL GROWTH OF INFANTS BORN BY CAESAREAN SECTION

FIELD OF THE INVENTION

The invention relates to nutrition for infants, in particular infant formula, intended to be used as a source of nutrition for infants born by Caesarean section.

BACKGROUND OF THE INVENTION

Human milk is the uncontested gold standard concerning infant nutrition. However, in some cases breastfeeding is inadequate or unsuccessful for medical reasons or because of a choice not to breastfeed. For such situations, infant or follow on formulas have been developed. Commercial infant formulas are commonly used today to provide supplemental or sole source of nutrition early in life. These formulas comprise a range of nutrients to meet the nutritional needs of the growing infant, and typically include fat, carbohydrate, protein, vitamins, minerals, and other nutrients helpful for optimal infant growth and development. Commercial infant formulas are designed to mimic, as closely as possible, the composition and function of human milk.

Since long it has been appreciated that breastfed infants have a different weight gain pattern or trajectory compared to formula-fed infants. After the first week of life, breastfed infants tend to lose more weight than formula-fed infants. Although breastfed infants take slightly longer to regain their birth weight, the weight gain patterns are similar between breastfed and formula-fed infants for the first 4 months of life. Breastfed infants tend to have slightly higher weight at 3 months age (Andres et al, 2013, J Pediatrics 163: 49-54). After about 4 months of age, the rate of weight gain diverges remarkably between breastfed and formula-fed infants. The difference in average weight at 12 months approximates up to 500-650 g (Dewey et al., 1993, Am J Clin Nutr 57: 140-145; Dewey et al, 1992 Pediatrics 89:1035). Li et al, 2010, Pediatrics 125:e1386-e1393 discloses that infants that are bottle-fed in early infancy are more likely to empty the bottle or cup in late infancy than those who are fed directly at the breast. Bottle-feeding, regardless of the type of milk, is distinct from feeding at the breast in its effect on infants' self-regulation of milk intake.

The worldwide rate of infant deliveries via Caesarean section has increased over the last decade, making it the most common surgical procedure performed in women of childbearing age today. While the WHO recommends that Caesarean section deliveries should be provided to those who need them only, in many countries the rate of Caesarean section deliveries significantly exceeds this recommendation. Over the past years, the medical field has started to become aware that a Caesarean section delivery introduces health risks, and the obstetrician is thus advised to assess these long and short-term health consequences for mother and infant, as well as weigh the risks associated with the procedure itself against not performing the procedure (Robson et al. MJA 206, 181-185, 2017).

Nowadays, Caesarean section delivery has been associated with delayed intestinal colonization by beneficial bacteria, impaired immune system, and increased risk of asthma and obesity in the infant. Huh et al., 2012, Arch Dis Child 97(7): 610-616 described that infants delivered by Caesarean section may be at increased risk of childhood obesity. This has been later studied e.g. by Mesquita et al., 2013, PLoS ONE 8(6):e66827, who compared peripheral and central adiposity in young adults born by Caesarean section and by vaginal delivery. Mesquita et al. found that the association of Caesarean section with adiposity was consistently observed. Mueller et al., 2015, Int J Obes 39(4):665-670 also observed that Caesarean section and exposure to antibiotics in the second or third trimester were associated with higher offspring risk of childhood obesity.

As indicated above, delivery via Caesarean section is a risk factor associated with obesity later in life. Obesity is a major health problem in the Western world. Breastfed infants have a decreased chance of becoming obese later in life, compared to standard formula fed infants. Early in life feeding has a lasting programming effect on such disease risks in adulthood. There is a need to provide improved infant nutrition that positively affects postnatal growth trajectory or body development in infants born via Caesarean section.

Human milk lipids are known have a distinct physical structure composed of large lipid globules with an average mode diameter of about 4 µm existing of a triglyceride core coated by a tri-layer of membranes, the milk fat globule membrane (MFGM). The diameter of lipid droplets in standard infant formula is typically about 0.3-0.5 µm due to the industrial processing procedures to achieve stable and reproducible end products. Standard infant formula lipid droplets are not surrounded by MFGM but mostly by proteins such as casein.

Infant formula with lipid globules with an architecture more similar to the lipid globules in human milk have been described. WO 2015/065193 describes nutritional compositions comprising specifically designed lipid globules for preterm infants, small for gestational age infants and infants with retarded growth due to physical or mental stress after birth, for promoting catch up growth and/or improved body composition. In WO 2012/173467 the use of a specifically designed lipid component with optimal fatty acid profile, an enhanced portion of the palmitic acid residues at the sn-2 position and the presence as lipid globules with a certain size and/or coating is described for an early in life diet for improving the development of a healthy body composition, in particular prevention of obesity, later in life. WO 2010/027258 and WO 2010/027259 describe infant formulae with large lipid globules coated with phospholipids for the prevention of obesity later in life. WO 2017/064304 describes the comparison of the growth trajectory of infants receiving infant formulae with large lipid globules coated with phospholipids with the growth trajectory of infants from the breastfed reference group when looking at weight and body mass index (BMI) at 12 months of age.

The present invention aims to provide infant nutrition with a lipid component beneficially affecting the postnatal growth trajectory or body development in an infant that is born via Caesarean section.

SUMMARY OF THE INVENTION

The inventors compared the postnatal body mass index (BMI) of groups of healthy term infants born either vaginally or by Caesarean section during the first 12 months of life with each other. One group received an experimental infant formula comprising a lipid component in the form of large lipid globules coated with phospholipids, and one group received a control infant formula without a lipid component in the form of large lipid globules coated with phospholipids, but in the form of standard lipid globules with a mode diameter based on volume of about 0.3-0.5 µm coated with protein. Both formulas were administered up to 17 weeks of life. The control and experimental milk formulas were similar in caloric content, as well as in lipid, carbohydrate and protein content.

It was found that when analysing the BMI for the whole study period up to 12 months of age the BMI gain of the group of infants that received the experimental formula was significantly lower than the BMI gain of the group of infants that received the control infant formula for both the infants that were born via Caesarean section and for infants that were born via vaginal delivery. Surprisingly it was found that the difference in BMI gain between the infants receiving the experimental and the control formula was about 3-fold higher in infants born via Caesarean section than in infants born via vaginal delivery. This measured difference was statistically significant different. Overall, the inventors thus surprisingly found a stronger effect of the experimental formula in infants that were born via Caesarean section compared to those born vaginally.

Hence, feeding an infant formula with a similar caloric content and macro-ingredient content but having a different architecture of lipid globules has a beneficial effect on the growth pattern or postnatal growth trajectory early in life, rendering it advantageously more similar to the growth pattern or trajectory early in life of breastfed infants. Yet it also has a differential effect in the sense that in infants born via Caesarean section the beneficial effect is more prominent compared to infants born via the vaginal route. Infants born via Caesarean section benefit to a larger extent from the nutritional intervention with the experimental formula compared to infants born via vaginal delivery for developing a desired growth trajectory or body development. Hence an improvement of the postnatal growth trajectory or body development is achieved in infants born via Caesarean section. Likewise, infants born via Caesarean section benefit for preventing or reducing the risk of an unbalanced postnatal growth trajectory or body development in such an infant being at risk of having an unbalanced postnatal growth trajectory or body development compared to the effect it has on infants born via vaginal delivery. Hence prevention or a reduction of the risk of an unbalanced postnatal growth trajectory or body development is achieved in infants born via Caesarean section.

DETAILED DESCRIPTION OF THE INVENTION

The present invention concerns a method for improving the postnatal growth trajectory or body development in an infant that is born via Caesarean section, said method comprising feeding said infant a nutritional composition selected from an infant formula and a follow-on formula comprising carbohydrates, protein and lipid, i) wherein the lipid comprises linoleic acid and alpha-linolenic acid in a weight ratio of 2 to 20, ii) the lipid comprises at least 10 wt. % palmitic acid based on total lipid, and at least 15 wt % of the palmitic acid is esterified to the sn-2 position of a triglyceride based on total palmitic acid, and wherein the nutritional composition comprises lipid globules that have a) a mode diameter based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipid.

In other words, the present invention concerns a nutritional composition selected from an infant formula and a follow on formula comprising carbohydrates, protein and lipid, wherein i) the lipid comprises linoleic acid and alpha-linolenic acid in a weight ratio of 2 to 20, ii) the lipid comprises at least 10 wt. % palmitic acid based on total lipid, and at least 15 wt % of the palmitic acid is esterified to the sn-2 position of a triglyceride based on total palmitic acid, and wherein the nutritional composition comprises lipid globules that have a) a mode diameter based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipid, for use in improving the postnatal growth trajectory or body development in an infant that is born via Caesarean section.

The invention can also be worded as the use of lipid globules in the manufacture of a nutritional composition selected from an infant formula and a follow on formula for use in improving the postnatal growth trajectory or body development in an infant that is born via Caesarean section, wherein the nutritional composition comprises carbohydrates, protein and lipid, wherein, i) the lipid comprises linoleic acid and alpha-linolenic acid in a weight ratio of 2 to 20, ii) the lipid comprises at least 10 wt. % palmitic acid based on total lipid, and at least 15 wt. % of this palmitic acid is esterified to the sn-2 position of a triglyceride based on total palmitic acid, and wherein the nutritional composition comprises lipid globules that have a) a mode diameter, based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipid.

It may be considered that improvement of the postnatal growth trajectory or body development in an infant that is born via Caesarean section encompasses a non-therapeutic effect. In view thereof, the present invention can also be considered as relating to a method for non-therapeutic improvement of the postnatal growth trajectory or body development in an infant that is born via Caesarean section by administration of a nutritional composition selected from an infant formula and a follow on formula comprising carbohydrates, protein and lipid, wherein i) the lipid comprises linoleic acid and alpha-linolenic acid in a weight ratio of 2 to 20, ii) the lipid comprises at least 10 wt. % palmitic acid based on total lipid, and at least 15 wt % of the palmitic acid is esterified to the sn-2 position of a triglyceride based on total palmitic acid, and wherein the nutritional composition comprises lipid globules that have a) a mode diameter based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipid The present invention concerns a method for preventing or reducing the risk of an unbalanced postnatal growth trajectory or body development in an infant at risk of having an unbalanced postnatal growth trajectory or body development, said infant being born via Caesarean section, said method comprising feeding said infant a nutritional composition selected from an infant formula and a follow-on formula comprising carbohydrates, protein and lipid, i) wherein the lipid comprises linoleic acid and alpha-linolenic acid in a weight ratio of 2 to 20, ii) the lipid comprises at least 10 wt. % palmitic acid based on total lipid, and at least 15 wt % of the palmitic acid is esterified to the sn-2 position of a triglyceride based on total palmitic acid, and wherein the nutritional composition comprises lipid globules that have a) a mode diameter based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipid.

The invention also concerns a nutritional composition selected from an infant formula and a follow on formula comprising carbohydrates, protein and lipid, wherein i) the lipid comprises linoleic acid and alpha-linolenic acid in a weight ratio of 2 to 20, ii) the lipid comprises at least 10 wt. % palmitic acid based on total lipid, and at least 15 wt % of the palmitic acid is esterified to the sn-2 position of a triglyceride based on total palmitic acid, and wherein the nutritional composition comprises lipid globules that have a) a mode diameter based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipid, for use in preventing or reducing the risk of an unbalanced postnatal growth trajectory or body development in an infant at risk of having an unbalanced postnatal growth trajectory or body development, said infant being born via Caesarean section.

The invention can also be worded as the use of lipid globules in the manufacture of a nutritional composition selected from an infant formula and a follow on formula for use in preventing or reducing the risk of an unbalanced postnatal growth trajectory or body development in an infant at risk of having an unbalanced postnatal growth trajectory or body development, said infant being born via Caesarean section, wherein the nutritional composition comprises carbohydrates, protein and lipid, wherein, i) the lipid comprises linoleic acid and alpha-linolenic acid in a weight ratio of 2 to 20, ii) the lipid comprises at least 10 wt. % palmitic acid based on total lipid, and at least 15 wt. % of this palmitic acid is esterified to the sn-2 position of a triglyceride based on total palmitic acid, and wherein the nutritional composition comprises lipid globules that have a) a mode diameter, based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipid.

Lipid Globules

According to the present invention, the nutritional composition comprises lipid globules. When in liquid form these lipid globules are emulsified in the aqueous phase. Alternatively the lipid globules are present in a powder and the powder is suitable for reconstitution with water or another food grade aqueous phase, preferably to provide a ready to drink formula. The lipid globules comprise a core and a surface. The core preferably comprises vegetable lipid and preferably comprises at least 90 wt. % triglycerides and more preferably essentially consists of triglycerides. Not all vegetable lipids that are present in the composition need necessarily be comprised in the core of lipid globules, but preferably a major part is, preferably more than 50% wt. %, more preferably more than 70 wt. %, even more preferably more than 85 wt. %, even more preferably more than 95 wt. %, most preferably more than 98 wt. % of the vegetable lipids that are present in the composition are comprised in the core of lipid globules. In one embodiment the core of the lipid globules comprises at least 40 wt. % triglycerides of vegetable origin, more preferably at least 50 wt. %, even more preferably at least 70 wt. % triglycerides of vegetable origin, more preferably the core of the lipid globules comprises at least 85 wt. %, more preferably at least 95 wt. % triglycerides of vegetable origin. The lipid globules in the nutritional composition in the method or use of the present invention have a volume-weighted mode diameter above 1.0 μm, preferably above 3.0 μm, more preferably 4.0 μm or above, preferably between 1.0 and 10 μm, more preferably between 2.0 and 8.0 μm, even more preferably between 3.0 and 8.0 μm, most preferably between 4.0 μm and 8.0 μm. Preferably in addition the size distribution is in such a way that at least 45 volume %, preferably at least 55 volume %, even more preferably at least 65 volume %, even more preferably at least 75 volume % has a diameter between 2 and 12 μm. More preferably at least 45 volume %, preferably at least 55 volume %, even more preferably at least 65 volume %, even more preferably at least 75 volume % has a diameter between 2 and 10 μm. Even more preferably at least 45 volume %, preferably at least 55 volume %, even more preferably at least 65 volume %, even more preferably at least 75 volume % has a diameter between 4 and 10 μm. Preferably less than 5 volume % has a diameter above 12 um.

The percentage of lipid globules is based on volume of total lipid. The mode diameter relates to the diameter which is the most present based on volume of total lipid, or the peak value in a graphic representation, having on the X—as the diameter and on the Y—as the volume (%).

The volume of the lipid globule and its size distribution can suitably be determined using a particle size analyzer such as a Mastersizer (Malvern Instruments, Malvern, UK), for example by the method described in Michalski et al, 2001, Lait 81: 787-796.

Phospholipids

The nutritional composition to be administered in the method or use according to the present invention comprises phospholipids, preferably the nutritional composition comprises phospholipids derived from mammalian milk, preferably derived from non-human mammalian milk. Phospholipids derived from non-human mammalian milk include phospholipids isolated from milk lipid, cream lipid, cream serum lipid, butter serum lipid beta serum lipid, whey lipid, cheese lipid and/or buttermilk lipid. The buttermilk lipid is typically obtained during the manufacture of buttermilk. The butter serum lipid or beta serum lipid is typically obtained during the manufacture of anhydrous milk fat from cream or butter. Preferably the phospholipids are obtained from milk cream. The phospholipids are preferably derived from milk of cows, mares, sheep, goats, buffalos, horses and camels, most preferably from cow's milk. It is most preferred to use a lipid extract isolated from cow's milk. A suitable source of phospholipids derived from non-human mammalian milk is the fraction that can be isolated from milk called milk fat globule membrane (MFGM). Hence in one embodiment, the phospholipids to be used in the nutritional composition in the method or use according to the present invention are derived from or form part of the milk fat globule membrane (MFGM), or are provided as MFGM, preferably cow's milk MFGM.

The nutritional composition comprises 0.5 to 20 wt. % phospholipids based on total lipid, more preferably 0.5 to 10 wt. %, more preferably 1 to 10 wt. %, even more preferably 2 to 10 wt. % even more preferably 3 to 8 wt. % phospholipids based on total lipid.

The lipid globules that are present in the nutritional composition for use according to the present invention are at least partly coated on the surface with phospholipids. By 'coating' is meant that the outer surface layer of the lipid globule comprises phospholipids, whereas these phospholipids are virtually absent in the core of the lipid globule. The presence of phospholipids as a coating or outer layer of the lipid globule in the diet administered was found to advantageously promote a growth trajectory or body development that is more similar to that of human milk fed infants. Not all phospholipids that are present in the composition need necessarily be comprised in the coating, but preferably a major part is.

Preferably more than 30 wt. %, more preferably more than 50 wt. %, more preferably more than 70 wt. %, even more preferably more than 85 wt. %, most preferably more than 95 wt. % of the phospholipids that are present in the composition are comprised in the coating of lipid globules. Preferably the phospholipids comprise at least 15 wt. % sphingomyelin based on total phospholipids.

According to the present invention, the nutritional composition preferably comprises glycerophospholipids. Glycerophospholipids are a class of lipids formed from fatty acids esterified at the hydroxyl groups on carbon-1 and carbon-2 of the backbone glycerol moiety and a negatively-charged phosphate group attached to carbon-3 of the glycerol via an ester bond, and optionally a choline group (in case of phosphatidylcholine, PC), a serine group (in case of phosphatidylserine, PS), an ethanolamine group (in case of phosphatidylethanolamine, PE), an inositol group (in case of phosphatidylinositol, PI) or a glycerol group (in case of phosphatidylglycerol, PG) attached to the phosphate group. Lysophospholipids are a class of phospholipids with one fatty acyl chain. Preferably the present composition contains PC, PS, PI and/or PE, more preferably at least PC.

Preferably the nutritional composition comprises sphingomyelin. Sphingomyelins have a phosphorylcholine or phosphorylethanolamine molecule esterified to the 1-hydroxy group of a ceramide. They are classified as phospholipid as well as sphingolipid, but are not classified as a glycerophospholipid nor as a glycosphingolipid. Preferably the nutritional composition comprises 0.05 to 10 wt. % sphingomyelin based on total lipid, more preferably 0.1 to 5 wt. %, even more preferably 0.2 to 2 wt. %.

According to the present invention, the nutritional composition preferably comprises cholesterol. The nutritional composition preferably comprises at least 0.005 wt. % cholesterol based on total lipid, more preferably at least 0.01 wt. %, more preferably at least 0.02 wt. %, more preferably at least 0.05 wt. %., even more preferably at least 0.1 wt. %. Preferably the amount of cholesterol does not exceed 10 wt. % based on total lipid, more preferably does not exceed 5 wt. %, even more preferably does not exceed 1 wt. % of total lipid.

Methods for obtaining lipid globules with an increased size and coating with phospholipids are disclosed in WO 2010/0027258, WO 2010/0027259 and WO 2013/135738.

Infant Formula and Follow on Formula

The nutritional composition to be administered in the method or use according to the present invention is selected from an infant formula and a follow on formula. This means that the present nutrition composition is not human milk. Alternatively the term "formula" means that it concerns a composition that is artificially made or in other words that it is synthetic. Hence in one embodiment the nutritional composition is selected from an artificial infant formula and an artificial follow on formula or a synthetic infant formula and a synthetic follow on formula. In the present context, infant formula refers to nutritional compositions, artificially made, intended for infants of 0 to about 4 to 6 months of age and are intended as a substitute for human milk. Typically infant formulas are suitable to be used as sole source of nutrition. Such formulas are also known as starter formula. Formula for infants starting with at 4 to 6 months of life to 12 months of life are intended to be supplementary feedings to infants that start weaning on other foods. Such formulas are also known as follow on formulas. Infant and follow on formulas are subject to strict regulations, for example for the EU Commission Directive 2006/141/EC.

The nutritional composition preferably comprises 3 to 7 g lipid/100 kcal, preferably 4 to 6 g lipid/100 kcal, more preferably 4.5 to 5.5 g lipid/100 kcal, 1.25 to 5 g protein/100 kcal, preferably 1.35 to 4 g protein/100 kcal, more preferably 1.5 to 3 g protein/100 kcal, more preferably 1.25 to 2.5 g protein/100 kcal, more preferably 1.25 to 2.25 g/100 kcal, even more preferably 1.25 to 2.1 g protein/100 kcal and 6 to 18 g digestible carbohydrate/100 kcal, preferably 8 to 16 g digestible carbohydrate/100 kcal, more preferably 10 to 15 g digestible carbohydrate/100 kcal. The nutritional composition to be administered in the method or use according to the present invention comprises carbohydrates, protein and lipids wherein preferably the lipids provide 30 to 60% of the total calories, the protein provides 5 to 20% of the total calories and the carbohydrates provide 25 to 75% of the total calories. Preferably the nutritional composition comprises 10 to 50 wt. % lipids based on dry weight of the total composition.

Lipid

Herein LA refers to linoleic acid and/or acyl chain (18:2 n6); ALA refers to α-linolenic acid and/or acyl chain (18:3 n3); PUFA refers to polyunsaturated fatty acids and/or acyl chains; MUFA refers to monounsaturated fatty acids and/or acyl chains; LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3). PA relates to palmitic acid and/or acyl chains (C16:0). Medium chain fatty acids (MCFAs) refer to fatty acids and/or acyl chains with a chain length of 6, 8 or 10 carbon atoms.

The lipid in the nutritional composition to be administered in the method or use according to the present invention preferably comprises vegetable lipids. The lipid that is present in the nutritional composition in the method or use according to the invention preferably comprises PUFAs, more preferably LC-PUFAs, as LC-PUFAs further improve the growth patterns and BMI development. The nutritional composition preferably comprises 5 to 35 wt. % PUFA, more preferably 10 to 30 wt. % PUFA, most preferably 15 to 20 wt. % PUFA, based on total lipid. In one embodiment the lipid in the nutritional composition for the method or use according to the invention comprises at least 10 wt. % polyunsaturated fatty acid based on total lipid. It is also preferred that the nutritional composition comprises MUFAs, preferably 10 to 80 wt. % MUFA, more preferably 20 to 70 wt. % MUFA, most preferably 35 to 55 wt. % MUFA, based on total lipid.

LA preferably is present in a sufficient amount in order to promote a healthy growth and development, yet in an amount as low as possible to prevent occurrence of unbalance in growth or body development. The nutritional composition therefore preferably comprises less than 20 wt. % LA based on total lipid, preferably less than 15 wt. % LA based on total lipid. Preferably, the nutritional composition comprises at least 5 wt. % LA based on total lipid, preferably the nutritional composition comprises 5 to 15 wt. % LA based on total lipid. Preferably, ALA is present in a sufficient amount to promote a healthy growth and development of the infant. The nutritional composition therefore preferably comprises at least 1.0 wt. % ALA based on total lipid. Preferably the nutritional composition comprises at least 1.5 wt. % ALA based on total lipid, more preferably at least 2.0 wt. %. Preferably the nutritional composition comprises less than 12.5 wt. % ALA, more preferably less than 10.0 wt. %, most preferably less than 5.0 wt. % ALA based on total lipid. Preferably the nutritional composition comprises 1 to 5 wt. % ALA based on total lipid. Preferably the nutritional composition comprises less than 15 wt. % linoleic acid and more than 1 wt. % alpha-linolenic acid based on total lipid. The nutritional composition comprises a weight ratio of LA/ALA from 2 to 20, more preferably from 3 to 16, more preferably from 4 to 14, more preferably from 5 to 12.

Preferably the nutritional composition comprises less than 10 wt. % short chain fatty acids based on total lipid, preferably less than 8 wt. %, preferably less than 6 wt. %, preferably less than 5 wt. %. Preferably the nutritional composition comprises at least 0.5 wt. % short chain fatty acids based on total lipid, preferably at least 0.6 wt. %, less than 8 wt. %, preferably at least 0.9 wt. %, more preferably at least 1.2 wt. %, more preferably at least 2.0 wt. %. Short chain fatty acids are fatty acids with an acyl chain of 2 to 6 carbon atoms. Preferably the nutritional composition comprises less than 10 wt. % butyric acid (acyl chain of 4 carbon atoms) based on total lipid, preferably less than 8 wt. %, preferably less than 6 wt. %, preferably less than 5 wt. %, preferably less than 4 wt. %. Preferably the nutritional composition comprises at least 0.5 wt. % butyric acid based on total lipid, preferably at least 0.6 wt. %, preferably at least 0.9 wt. %, more preferably at least 1.2 wt. %. The nutritional composition preferably comprises at least 3 wt. % MCFA based on total lipid, more preferably at least 10 wt. %, even more preferably 15 wt. %. The present composition advantageously comprises less than 50 wt. % MCFA based on total lipid, more preferably less than 30 wt. %, even more preferably less than 20 wt. %.

According to the present invention, the nutritional composition preferably comprises LC-PUFA, more preferably n-3 LC-PUFA, since n-3 LC-PUFA promote an advantageous growth trajectory. More preferably, the nutritional composition comprises EPA, DPA and/or DHA, even more preferably DHA. Since a low concentration of DHA, DPA and/or EPA is already effective and normal growth and development are important, the content of n-3 LC-PUFA in the nutritional composition, more preferably DHA, preferably does not exceed 15 wt. % of the total lipid content, preferably does not exceed 10 wt. %, even more preferably does not exceed 5 wt. %. Preferably the nutritional composition comprises at least 0.15 wt. %, preferably at least 0.35 wt. %, more preferably at least 0.75 wt. %, n-3 LC-PUFA, more preferably DHA, of the total lipid content. In one embodiment, the present composition comprises at least 0.15 wt. % n-3 LC-PUFA based on total lipid selected from the group consisting of DHA, EPA, and DPA, more preferably DHA.

As the group of n-6 fatty acids, especially arachidonic acid (ARA) and LA as its precursor, counteracts the group of n-3 fatty acids, especially DHA and EPA and ALA as their precursor, the nutritional composition comprises relatively low amounts of ARA. The n-6 LC-PUFA, more preferably ARA, content preferably does not exceed 5 wt. %, more preferably does not exceed 2.0 wt. %, more preferably does not exceed 0.75 wt. %, even more preferably does not exceed 0.5 wt. %, based on total lipid. As the presence of ARA is not necessary for promoting a growth trajectory or BMI development similar to that of human milk fed infants, ARA may also be absent.

Palmitic Acid at Sn-2 Position of Triglyceride

The lipid in the nutritional composition to be administered in the method or use according to the present invention comprises triglycerides. Triglycerides comprise a glyceride molecule to which, via ester bonds, three fatty acid residues are attached, which may be the same or different, and which are generally chosen from saturated and unsaturated fatty acids containing 6 to 26 carbon atoms, including but not limited to LA, ALA, oleic acid (C18:1), PA and/or stearic acid (C18:0). Preferably the nutritional composition comprises at least 70 wt. %, more preferably at least 80 wt. %, more preferably at least 85 wt. % triglycerides, even more preferably at least 90 wt. % triglycerides based on total lipids. The fatty acid triglycerides may differ in the fatty acid residues that are present and/or in the respective position(s) of the fatty acid residues, e.g. in the sn-1, -2 and/or -3 position. The triglycerides used in the nutritional composition are chosen such that the amount of PA residues that are present in the triglycerides are 10 wt. % or more based on total fatty acid present in the triglycerides, preferably more than 15 wt. %. The nutritional composition in the method or use according to the invention comprises lipid that comprises at least 10 wt. % palmitic acid based on total lipid, and wherein at least 15% of the palmitic acid is present at the sn-2 position of the triglycerides, preferably at least 30% of the palmitic acid is present at the sn-2 position of the triglycerides. Preferably the amount of PA residues that are present in the triglycerides are below 30 wt. %, more preferably in the range of 16 to 24%. Preferably the triglycerides used in the nutritional composition are chosen such that of the total PA residues present in the triglyceride at least 20%, more preferably at least 30%, even more preferably at least 35%, and most preferably at least 40% are in the sn-2 or beta position of the triglyceride.

Suitable triglycerides for the nutritional composition in the method or use according to the invention are commercially available, e.g. from Loders Croklaan under the name Betapol™ and/or can be prepared in a manner known per se, for instance as described in EP 0 698 078 and/or EP 0 758 846. Another suitable source is InFat™ of Enzymotec. In case these lipids are obtained by trans- or interesterification of vegetable triglycerides, these sources are in the context of the present invention regarded as vegetable lipids. Preferably the amount of the triglyceride with increased amount of palmitic acid residues on the sn-2 position of a triglyceride molecule that is comprised in the lipid fraction of the composition that is to be administered according to the present method or use, ranges from 10 to 100 wt. %, preferably from 20 to 100 wt. %, more preferably from 20 to 80 wt. %, even more preferably from 50 to 80 wt. %.

A preferred source for triglycerides having palmitic acid at the sn-2 or beta position of the triglyceride is non-human animal lipid, more preferably non-human mammalian milk lipid, even more preferably cow's milk lipid. Preferably non-human mammalian milk lipid, in particular cow's milk lipid, is preferably derived from the group consisting of butter, butter fat, butter oil, and anhydrous milk fat, more preferably anhydrous milk fat and butter oil. Preferably the source of the milk lipid is in a homogenous fat phase, such as butter oil or anhydrous milk fat, and not in the form of oil in water emulsion such as cream, since the lipid globules of the present nutritional composition can be more easily prepared when in a homogenous fat phase. Preferably the amount of milk lipid ranges from 10 to 100 wt. % based on total lipid, preferably from 10 to 80 wt. % based on total lipid, more preferably from 10 to 70 wt. %, more preferably from 20 to 80 wt. %, more preferably from 15 to 60 wt. %, more preferably from 20 to 60 wt. %, even more preferably from 25 to 50 wt. % based on total lipid.

In an alternative embodiment, the present invention concerns a method for improving the postnatal growth trajectory or body development in an infant that is born via Caesarean section, said method comprising feeding said infant a nutritional composition selected from an infant formula and a follow-on formula comprising carbohydrates, protein and lipid,
i) wherein the lipid comprises linoleic acid and alpha-linolenic acid in a weight ratio of 2 to 20, and
ii) the lipid comprises 10 to 70 wt. % based on total lipid of non-human mammalian milk lipid derived from the group consisting of butter, butter fat, butter oil, and anhydrous milk fat, and wherein the nutritional composition comprises lipid globules that have
a) a mode diameter, based on volume of at least 1.0 μm and/or a diameter of 2 to 12 μm in an amount of at least 45 volume % based on total lipid and
b) the lipid globules are at least partly coated on the surface with phospholipids, the amount of phospholipids present in the nutritional composition being from 0.5 to 20 wt. % phospholipids based on total lipids.

In other words, in an alternative embodiment, the present invention concerns a nutritional composition selected from an infant formula and a follow on formula comprising carbohydrates, protein and lipid, wherein
i) the lipid comprises linoleic acid and alpha-linolenic acid in a weight ratio of 2 to 20,
ii) the lipid comprises 10 to 70 wt. % based on total lipid of non-human mammalian milk lipid derived from the group consisting of butter, butter fat, butter oil, and anhydrous milk fat, and wherein the nutritional composition comprises lipid globules that have
a) a mode diameter, based on volume of at least 1.0 μm and/or a diameter of 2 to 12 μm in an amount of at least 45 volume % based on total lipid and
b) the lipid globules are at least partly coated on the surface with phospholipids, the amount of phospholipids present in the nutritional composition being from 0.5 to 20 wt. % phospholipids based on total lipids,
for use in improving the postnatal growth trajectory or body development in an infant that is born via Caesarean section.

The invention in an alternative embodiment can also be worded as the use of lipid globules in the manufacture of a nutritional composition selected from an infant formula and a follow on formula for use in improving the postnatal growth trajectory or body development in an infant that is born via Caesarean section, wherein the nutritional composition comprises carbohydrates, protein and lipid, wherein,
i) the lipid comprises linoleic acid and alpha-linolenic acid in a weight ratio of 2 to 20,
ii) the lipid comprises 10 to 70 wt. % based on total lipid of non-human mammalian milk lipid derived from the group consisting of butter, butter fat, butter oil, and anhydrous milk fat, and wherein the nutritional composition comprises lipid globules that have
a) a mode diameter, based on volume of at least 1.0 μm and/or a diameter of 2 to 12 μm in an amount of at least 45 volume % based on total lipid and
b) the lipid globules are at least partly coated on the surface with phospholipids, the amount of phospholipids present in the nutritional composition being from 0.5 to 20 wt. % phospholipids based on total lipids.

The present invention concerns in an alternative embodiment a method for preventing or reducing the risk of an unbalanced postnatal growth trajectory or body development in an infant at risk of having an unbalanced postnatal growth trajectory or body development, said infant being born via Caesarean section, said method comprising feeding said infant a nutritional composition selected from an infant formula and a follow on formula comprising carbohydrates, protein and lipid,
i) wherein the lipid comprises linoleic acid and alpha-linolenic acid in a weight ratio of 2 to 20,
ii) the lipid comprises 10 to 70 wt. % based on total lipid of non-human mammalian milk lipid derived from the group consisting of butter, butter fat, butter oil, and anhydrous milk fat, and wherein the nutritional composition comprises lipid globules that have
a) a mode diameter, based on volume of at least 1.0 μm and/or a diameter of 2 to 12 μm in an amount of at least 45 volume % based on total lipid and
b) the lipid globules are at least partly coated on the surface with phospholipids, the amount of phospholipids present in the nutritional composition being from 0.5 to 20 wt. % phospholipids based on total lipids.

The invention in an alternative embodiment also concerns a nutritional composition selected from an infant formula and a follow on formula comprising carbohydrates, protein and lipid, wherein
i) the lipid comprises linoleic acid and alpha-linolenic acid in a weight ratio of 2 to 20,
ii) the lipid 10 to 70 wt. % based on total lipid of non-human mammalian milk lipid derived from the group consisting of butter, butter fat, butter oil, and anhydrous milk fat, and wherein the nutritional composition comprises lipid globules that have a) a mode diameter, based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipids, for use in preventing or reducing the risk of an unbalanced postnatal growth trajectory or body development in an infant at risk of having an unbalanced postnatal growth trajectory or body development, said infant being born via Caesarean section.

The invention in an alternative embodiment can also be worded as the use of lipid globules in the manufacture of a nutritional composition selected from an infant formula and a follow on formula for use in preventing or reducing the risk of an unbalanced postnatal growth trajectory or body development in an infant at risk of having an unbalanced postnatal growth trajectory or body development, said infant being born via Caesarean section, wherein the nutritional composition comprises carbohydrates, protein and lipid, wherein, i) the lipid comprises linoleic acid and alpha-linolenic acid in a weight ratio of 2 to 20, ii) the lipid comprises 10 to 70 wt. % based on total lipid of non-human mammalian milk lipid derived from the group consisting of butter, butter fat, butter oil, and anhydrous milk fat, and wherein the nutritional composition comprises lipid globules that have a) a mode diameter, based on volume of at least 1.0 μm and/or a diameter of 2 to 12 μm in an amount of at least 45 volume % based on total lipid and b) the lipid globules are at least partly coated on the surface with phospholipids, the amount of phospholipids present in the nutritional composition being from 0.5 to 20 wt. % phospholipids based on total lipids.

Non-human mammalian milk lipid in the present invention refers to all lipid components of milk, as produced by the mammalians, such as the cow, and is found in commercial milk and milk-derived products.

Butter in the present invention is a water-in-oil emulsion comprised of over 80 wt. % milk lipid.

Butterfat in the present invention relates to all of the lipid components in milk that are separable by churning, in other words, present in butter.

Anhydrous milk fat (AMF) is a term known in the art and relates to extracted milk lipid. Typically AMF comprises more than 99 wt. % lipid based on total weight. It can be prepared from extracting milk lipid from cream or butter. Anhydrous butter oil in the present invention is synonymous with AMF.

Butter oil also is a term known in the art. It typically relates to a milk lipid extract with more than 98 wt. % lipid and typically is a precursor in the process of preparing anhydrous milk fat or anhydrous butter oil.

Preferably the non-human mammalian milk comprises at least 70 wt. % triglycerides, more preferably at least 90 wt. %, more preferably at least 97 wt. %.

Preferably the non-human mammalian milk lipid is anhydrous milk fat or butter oil. Such milk fat lipid sources are high in triglyceride levels. Furthermore these lipid sources are in the form of a continuous fat phase or a water-in-oil emulsion form and not in the form of oil in water emulsion such as cream, since the lipid globules of the present nutritional composition can be more easily prepared when in a homogenous fat phase.

Preferably the amount of non-human mammalian milk lipid ranges from 10 to 70 wt. % based on total lipid, preferably ranges from 20 to 70 wt. %, more preferably from 15 to 60 wt. %, more preferably from 20 to 60 wt. %, even more preferably from 25 to 50 wt. % based on total lipid.

Protein

The nutritional composition comprises proteins, preferably in the amounts specified above. Preferably the protein provides 5 to 9% of the total calories of the nutritional composition. The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof and may include α-lactalbumin and β-lactoglobulin. More preferably, the protein source is based on acid whey or sweet whey from which caseino-glyco-macropeptide (CGMP) has been removed. Preferably the composition comprises at least 3 wt. % casein based on dry weight. Preferably the casein is intact and/or non-hydrolyzed. For the present invention protein includes peptides and free amino acids.

Digestible Carbohydrates

The nutritional composition comprises digestible carbohydrate, preferably in the amounts specified above. Preferred digestible carbohydrate sources are lactose, glucose, sucrose, fructose, galactose, maltose, starch and maltodextrin. Lactose is the main digestible carbohydrate present in human milk. Lactose advantageously has a low glycemic index. The nutritional composition preferably comprises lactose. The nutritional composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the present composition preferably comprises at least 25 wt. % lactose, preferably at least 40 wt. %.

Non Digestible Carbohydrates

In one embodiment the nutritional composition comprises non-digestible oligosaccharides. Preferably the nutritional composition comprises non-digestible oligosaccharides with a degree of polymerization (DP) between 2 and 250, more preferably 3 and 60.

Preferably the present composition comprises fructo-oligosaccharides, inulin and/or galacto-oligosaccharides, more preferably galacto-oligosaccharides, most preferably trans-galacto-oligosaccharides. In a preferred embodiment the composition comprises a mixture of transgalacto-oligosaccharides and fructo-oligosaccharides or inulin. Suitable non-digestible oligosaccharides are for example Vivinal® GOS (FrieslandCampina DOMO), RaftilinHP® or Raftilose® (Orafti).

Preferably, the nutritional composition comprises of 80 mg to 2 g non-digestible oligosaccharides per 100 ml, more preferably 150 mg to 1.50 g, even more preferably 300 mg to 1 g per 100 ml. Based on dry weight, the nutritional composition preferably comprises 0.25 wt. % to 20 wt. %, more preferably 0.5 wt. % to 10 wt. %, even more preferably 1.5 wt. % to 7.5 wt. %.

Application

In the method or use according to the present invention, a nutritional composition is administered to an infant or is used in an infant that is born via Caesarean section. In the context of the present invention an infant has an age up to 12 months. Preferably the nutritional composition is administered to or is used in a term born infant. A term infant means an infant born art a gestational age of 37 to 42 weeks. Preferably the nutritional composition is administered to or is used in a healthy infant. Preferably the nutritional composition is used at least during the first 2 months of life, preferably at least during the first 3 months of life of the infant, more preferably at least during the first 4 months of life of the infant. Preferably the nutritional composition is administered to an infant with an age below 6 months, more preferably below 4 months of age.

According to the present invention the postnatal growth trajectory or body development in an infant that is born via Caesarean section is improved. Preferably the growth trajectory or body development is the trajectory or development of body mass index (BMI), preferably the trajectory or development body mass index (BMI) is the first 4 months of life of the infant, more preferably the trajectory or development body mass index (BMI) is the first 12 months of life of the infant. In one embodiment, improving the postnatal growth trajectory or body development of the infant is reducing the increase of BMI of the infant. Preferably the improvement is compared to the postnatal growth trajectory or body development in an infant born via vaginal delivery, preferably an infant born via vaginal delivery fed the infant formula or follow on formula as defined according to the present invention. Preferably for a proper comparison the age of the infant and time period over which the nutritional composition is administered correspond.

According to the present invention an unbalanced postnatal growth trajectory or body development in an infant at risk of having an unbalanced postnatal growth trajectory or body development, said infant being born via Caesarean section is prevented or the risk thereof is reduced. Preferably the growth trajectory or body development is the trajectory or development of body mass index (BMI), preferably the trajectory or development body mass index (BMI) in the first 4 months of life of the infant, preferably the trajectory or development body mass index (BMI) in the first 12 months of life of the infant. Preferably the prevention or reduction of the risk is compared to the postnatal growth trajectory or body development in an infant born in an infant born via vaginal delivery, preferably an infant born via vaginal delivery fed the infant formula or follow on formula as defined according to the present invention. Preferably for a proper comparison the age of the infant and time period over which the nutritional composition is administered correspond.

Preferably the infant formula or follow on formula, when ready to drink has an energy density of 60 kcal to 75 kcal/100 ml, more preferably 60 to 70 kcal/100 ml. This density ensures an optimal balance between hydration and caloric intake.

In one embodiment, the infant formula or follow on formula is a powder. Suitably, the infant formula or follow on formula is in a powdered form, which can be reconstituted with water or other food grade aqueous liquid, to form a ready-to drink liquid, or is in a liquid concentrate form that should be diluted with water to a ready-to-drink liquid. It was found that lipid globules maintained their size and coating when reconstituted.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1: Test and Control Formula

Diet 1: Control Infant Formula (Control Formula)

The Control formula comprised per 100 ml ready to drink formula 66 kcal, 1.3 g protein (whey protein and casein in a 6/4 w/w ratio), 7.3 g digestible carbohydrates (mainly lactose), 3.4 g fat and 0.8 g short chain galacto-oligosaccharides (source Vivinal® GOS) and long chain fructo-oligosaccharides (source RaftilinHP®) in a 9/1 w/w ratio, and minerals, vitamins, trace elements and other micronutrients in compliance with directives for infant formula. The formula is provided as a powder with the instruction to reconstitute with water, about 13.6 g powder is to be reconstituted to obtain a 100 ml ready to drink infant formula.

The fat component comprised mainly vegetable fat (blend of palm oil, low erucic acid rape seed oil, coconut oil, high oleic sunflower oil, sunflower oil, a small amount of soy lecithin (0.13 wt. %) and about 1.5 wt. % of an LC-PUFA premix (fish oil and microbial oil).

The fat component was present in the form of lipid globules and the lipid globules had a mode diameter, based on volume, of about 0.5 µm, and the volume % of lipid globules with a mode between 2 and 12 µm was below 10 vol. %.

Diet 2: Test Infant Formula (Test Formula)

The Test formula was an infant formula similar to Diet 1, except for the following differences:

The lipid globules in the Test formula had a mode diameter, based on volume, of about 5.6 µm, and the volume % of lipid globules with a mode between 2 and 12 µm was above 45 vol. %.

The fat component consisted of about 51 wt. % vegetable fat (blend of low erucic acid rape seed oil, coconut oil, high oleic sunflower oil, sunflower oil), about 44 wt. % bovine anhydrous milk fat, 1.5 wt. % LC-PUFA containing oil (fish oil and microbial oil), 0.13 wt. % soy lecithin, about 3.6 wt. % milk fat derived from buttermilk rich in milk phospholipids or milk fat globule membranes (milk phospholipids were about 1.5 wt. % based on total lipid).

The fatty acid composition was very similar between diet 1 and 2, in saturated, mono unsaturated and poly unsaturated acids, and in n3 and n6 PUFA content. The amount of palmitic acid was 18.4 wt. % and 17.7 wt. % (based on total lipid) for diet 1 and 2, respectively. For diet 2 about 36 wt. % of the palmitic acid residues was in the sn2 position, while for diet 1 this was about 13 wt. %. The amount of C4:0 (butyric acid) was 0.10 wt. % in diet 1 and 1.39 wt. % in diet 2, C6:0 (caproic acid) was 0.24 wt. % in diet 1 and 0.98 wt. % in diet 2. The wt. % are based on total lipid in the infant formula, unless indicated otherwise.

Example 2: Study Protocol and Study Population

After parent(s)/legal guardian(s) have signed informed consent, exclusively formula fed infants, eligible for participation, were randomised to receive either the Test Formula (Diet 2) or the Control formula (Diet 1) for a double-blind period of maximally 4 months (depending on their age at study entry). Exclusively breastfed infants participated in the reference group and had the same visit schedule and study assessments as the randomised infants.

At the first visit, baseline and birth data were collected, as well as maternal baseline information, and the study product and diaries were provided to the parent(s). Study visits were conducted at 4 and 12 months of age. Information and anthropometrical measurements were collected during the visits. During the visit at 12 months, anthropometrical measurements were collected.

In total 4 countries with 17 sites participated in the study, and in total 313 subjects were enrolled; 6 sites in the Netherlands (121 subjects), 3 sites in France (13 subjects), 7 sites in Belgium (158 subjects), and 1 site in Singapore (21 subjects). Of the total of 313 enrolled subjects, 223 were randomised and 88 were included in the breastfed reference group, 2 subjects were screen failures and were consequently not randomised.

The All-Subjects-Treated (AST) data set consisted of all subjects randomised (ASR, n=223) who received at least some study product. Subjects (n=8), with sufficient evidence that no study product was consumed, were considered as non-treated, and were not included in the AST group (n=215).

The ITT data set consisted of all subjects from the ASR group (ITT=ASR). Results from the ITT analysis reflect the effects on the targeted population in a real clinical situation/estimates the effect (effectiveness) of the treatment policy. Subjects' data were analysed 'as randomised' (n=223).

A Per-Protocol (PP) analysis restricts the analysis to the subjects who fulfil the protocol in the terms of eligibility, interventions, instructions/restrictions and outcome assessment. The PP data set consisted of all subjects and/or subjects' visits from the ITT data set without any major protocol deviations (n=174). Thus, the PP dataset was not limited to subjects who completed the study, and the number of subjects per visits varies. Results from the PP analysis estimate the effect (efficacy) of the treatment. Subjects' data were analysed 'as treated'.

The following rules have been applied for exclusion of subjects from the PP data set: Age at baseline (=visit 1)>35 days, birth weight missing or is <9.96th or >90.04th percentile (based on WHO Child growth standard references), head circumference at inclusion is outside ±2.04 SD percentile (based on WHO Child growth standard references), not having at least one valid post-baseline visit. Study product consumption started ≥6 days after baseline, having received a different study product as his/her twin sibling, no study product was consumed, relevant medical history, i.e. illnesses/conditions as identified by the Medical Monitor. The following rules have been applied for exclusion of distinct visits from the PP data set: Any visit >3 days after stop of study product intake with the exception of the visit at 12 months, regardless if stop was temporarily or not, any visit >3 days after start of other formula feeding, any visit >3 days after start of solid feeding. 49 randomised subjects plus certain visits were excluded.

For the non-randomised breastfed reference group data sets corresponding to the ITT and PP populations of the randomised infants have been defined, too. Correspondingly to the ITT data set, a full breastfed group (FBF) has been defined, no breastfed subjects were excluded (n=88). Correspondingly to the PP dataset, a Protocol Compliant Breastfed Reference (PCBF) data set has been defined, applying the relevant rules as defined for the PP dataset (n=77). The following rules have been applied for exclusion of subjects from the PCBF data set: Age at baseline >35 days, birth weight missing or is <9.96th or >90.04th percentile (based on WHO Child growth standard references), head circumference at inclusion is outside ±2.04 SD (based on WHO Child growth standard references), not having at least one valid post-baseline visit, or relevant medical history, i.e. illnesses/conditions as identified by the Medical Monitor. The following rules have been applied for exclusion of distinct visits from the PCBF data set: Any visit >3 days after stop of breastfeeding, in case stop of breastfeeding occurred before 13 weeks of age, any visit >3 days after start of other formula feeding, in case start of other formula feeding occurred before 13 weeks of age, any visit >3 days after start of solid feeding, in case start of other solid feeding occurred before visit 4. 11 breastfed subjects plus certain visits were excluded.

Subjects (either randomised or breastfed) who were included in PP/PCBF dataset up and including visit at 4 months of age and participated in the optional extension, were included in PP dataset at visit at 12 months.

There were no statistical significant differences between the intervention groups within the different datasets (PP, ITT) on the stratification factors sex, age at baseline (≤4 days/>14 days), regions (Europe vs. Asia). There was no difference in the study duration between the intervention groups.

Table 1 provides a tabular overview of the ITT population, showing the number and percentage of subjects by type of delivery, being vaginal or by Caesarean section, for the Test formula and Control formula and breastfed group. Table 2 provides a similar overview for the PP population.

TABLE 1

Study population statistics for the type of delivery of the ITT population.

|  | Test (n = 115) | Control (n = 108) |
|---|---|---|
| Type of delivery (n (%)): | | |
| Vaginal | 76 (66.09%) | 85 (78.70%) |
| Caesarean | 39 (33.91%) | 23 (21.30%) |

TABLE 2

Study population statistics for the type of delivery of the PP population.

|  | Test (n = 91) | Control (n = 83) |
|---|---|---|
| Type of delivery (n (%)): | | |
| Vaginal | 57 (62.64%) | 63 (75.90%) |
| Caesarean | 34 (37.36%) | 20 (24.10%) |

At baseline, the BMI (kg/m$^2$) of the vaginally-delivered infants or the Caesarean-delivered infants was comparable. The BMI of these randomised infants was also comparable to the breastfed reference group in the PP and ITT population. At 12 months the BMI of the infants that received the Test formula is more close to the BMI of the breastfed reference group, compared to the infants that received the Control formula in both the PP and ITT population.

The BMI gain, calculated as change from baseline to 4 months and as change from baseline to 12 months of age and was compared between the randomised groups (Test minus Control) separately for the group of infants born via Caesarean section and the group of infants born vaginally. A Parametric Growth Curve (PGC) model was applied, considering the overall study period (baseline until 12 months)

and correcting for stratification factors as described herein before. All statistical analyses were performed by Nutricia Research Utrecht using SAS® (SAS Enterprise Guide 4.3 or higher) for Windows, SAS Institute Inc., Cary, N.C. This approach assumes a parametric function of time (i.e. age of subject) and thus, describes the development of growth parameters (i.e. BMI) over time by a second order polynomial function. It does not require the study subjects to be measured at the same time points. The resulting parameters are compared to assess differences between the curves.

Tables 3 and 4 (ITT and PP population respectively) show the Least Squares (LS) mean estimate for the difference between groups (Test minus Control) in BMI gain per age interval and type of delivery. Infants that received the Control formula have a higher increase in BMI when compared to infants receiving Test formula. Surprisingly, in infants born via Caesarean section this difference was about 3-fold higher than in infants born via vaginal delivery which reached statistical significance already at 4 months for PP and at 12 months for PP and ITT.

TABLE 3

Differences in BMI gain (kg/m$^2$) between the Test and Control group for the different types of delivery for the ITT study population.

| | Age interval | Type of delivery | LS mean (SE) | P-value |
|---|---|---|---|---|
| Test minus Control | Baseline to 4 months | Vaginal | −0.218 (0.237) | 0.359 |
| | | Caesarean | −0.667 (0.372) | 0.074 |
| Test minus Control | Baseline to 12 months | Vaginal | −0.632 (0.278) | 0.024 |
| | | Caesarean | −1.481 (0.409) | <0.001 |

TABLE 4

Differences in BMI gain (kg/m$^2$) between the Test and Control group for the for the types of delivery for the PP study population.

| | Age interval | Type of delivery | LS mean (SE) | P-value |
|---|---|---|---|---|
| Test minus Control | Baseline to 4 months | Vaginal | −0.320 (0.269) | 0.236 |
| | | Caesarean | −1.045 (0.420) | 0.014 |
| Test minus Control | Baseline to 12 months | Vaginal | −0.617 (0.326) | 0.060 |
| | | Caesarean | −1.859 (0.475) | <0.001 |

Overall, the results are indicative for a stronger effect of the Test formula, when fed to infants born via Caesarean section, on promoting a postnatal growth trajectory or body development in an infant towards a more beneficial growth trajectory or body development (which is more similar to the growth trajectory or body development observed in infants which are breastfed) compared to the effect it has on infants born via vaginal delivery. Infants born via Caesarean section benefit to a larger extent from the nutritional intervention compared to infants born via vaginal delivery for developing a desired growth trajectory or body development. Hence an improvement of the postnatal growth trajectory or body development is achieved in infants born via Caesarean section. Also these results are indicative for a stronger effect of the Test formula when fed to infants born via Caesarean section, on preventing or reducing the risk of an unbalanced postnatal growth trajectory or body development in such an infant being at risk of having an unbalanced postnatal growth trajectory or body development compared to the effect it has on infants born via vaginal delivery. Hence prevention or a reduction of the risk of an unbalanced postnatal growth trajectory or body development is achieved in infants born via Caesarean section.

In particular the improvement of the postnatal growth trajectory or body development or prevention in infants born via Caesarean section is found when compared to the growth trajectory or body development in infants born via vaginal delivery and that were fed the same nutritional composition.

In particular the prevention or reduction of the risk of an unbalanced postnatal growth trajectory or body development in infants born via Caesarean section is found when compared to the growth trajectory or body development in infants born via vaginal delivery and that were fed the same nutritional composition.

The invention claimed is:

1. A method for non-therapeutic improvement of the postnatal growth trajectory or body development in an infant that is born via Caesarean section by administration of a nutritional composition selected from an infant formula and a follow on formula comprising carbohydrates, protein and lipid, wherein
  i) the lipid comprises linoleic acid and alpha-linolenic acid in a weight ratio of 2 to 20,
  ii) the lipid comprises at least 10 wt. % palmitic acid based on total lipid, and at least 15 wt. % of the palmitic acid is esterified to the sn-2 position of a triglyceride based on total palmitic acid,
  and wherein the nutritional composition comprises lipid globules that have
  a) a mode diameter based on volume of at least 1.0 μm and/or a diameter of 2 to 12 μm in an amount of at least 45 volume % based on total lipid and
  b) the lipid globules are at least partly coated on the surface with phospholipids, the amount of phospholipids present in the nutritional composition being from 0.5 to 20 wt. % phospholipids based on total lipid
  wherein the improvement of the postnatal growth trajectory or body development in infants born via Caesarean section is found when comparing to the growth trajectory or body development in infants born via vaginal delivery and that were fed the same nutritional composition.

2. The method for non-therapeutic improvement of the postnatal growth trajectory or body development according to claim 1 comprising less than 15 wt. % linoleic acid and more than 1 wt. % alpha-linolenic acid based on total fatty acids.

3. The method for non-therapeutic improvement of the postnatal growth trajectory or body development according to claim 1, wherein the growth trajectory or body development is the trajectory or development of body mass index (BMI).

4. The method for non-therapeutic improvement of the postnatal growth trajectory or body development according to claim 1, wherein the method results in reducing the increase of BMI of the infant.

5. The method for non-therapeutic improvement of the postnatal growth trajectory or body development according to claim 1, wherein the growth trajectory or body development is the trajectory or development of body mass index (BMI) in the first 12 months of life of the infant.

6. The method for non-therapeutic improvement of the postnatal growth trajectory or body development according to claim 1 claims, wherein the infant is a term born infant.

7. The method for non-therapeutic improvement of the postnatal growth trajectory or body development according to claim 1, wherein the phospholipids comprise at least 15 wt. % sphingomyelin based on total phospholipids.

8. The method for non-therapeutic improvement of the postnatal growth trajectory or body development according to claim 1, wherein the nutritional composition comprises phospholipids that are derived from or form part of the milk fat globule membrane (MFGM), or are provided as MFGM.

9. The method for non-therapeutic improvement of the postnatal growth trajectory or body development according to claim 1, wherein the nutritional composition comprises 0.5 to 20 wt. % phospholipids derived from mammalian milk based on total lipid.

10. The method for non-therapeutic improvement of the postnatal growth trajectory or body development according to claim 1, wherein at least 30 wt. % of the palmitic acid is esterified to the sn-2 position of a triglyceride based on total palmitic acid.

11. The method for non-therapeutic improvement of the postnatal growth trajectory or body development according to claim 1, wherein the lipid globules have a core comprising at least 40 wt. % of triglycerides of vegetable origin.

12. The method for non-therapeutic improvement of the postnatal growth trajectory or body development according to claim 1, wherein the composition is a powder, suitable to reconstitute with water to a ready to drink formula.

13. The method for non-therapeutic improvement of the postnatal growth trajectory or body development according to claim 8, wherein the fat globule membrane (MFGM) is cow's milk MFGM.

\* \* \* \* \*